(12) United States Patent
Tang et al.

(10) Patent No.: US 8,262,988 B2
(45) Date of Patent: Sep. 11, 2012

(54) ANTIGEN SUPPLY DEVICE

(75) Inventors: Huaipeng Tang, Tokyo (JP); Akihiro Seta, Tokyo (JP); Minoru Okuda, Yokohama (JP); Kazuhiro Hashigucci, Machida (JP); Kimihiro Okubo, Tokyo (JP)

(73) Assignee: Shinryo Corporation, Tokyo (JP)

( * ) Notice: Subject to any disclaimer, the term of this patent is extended or adjusted under 35 U.S.C. 154(b) by 959 days.

(21) Appl. No.: 12/088,520

(22) PCT Filed: Sep. 28, 2005

(86) PCT No.: PCT/JP2005/017866
§ 371 (c)(1),
(2), (4) Date: Mar. 28, 2008

(87) PCT Pub. No.: WO2007/037001
PCT Pub. Date: Apr. 5, 2007

(65) Prior Publication Data
US 2009/0155146 A1    Jun. 18, 2009

(51) Int. Cl.
*F24F 7/06*    (2006.01)
*B01L 3/00*    (2006.01)
(52) U.S. Cl. ............ 422/50; 422/402; 454/15; 454/39; 454/237; 454/228; 454/187; 118/326; 277/634
(58) Field of Classification Search .............. 454/223, 454/187; 55/385.2; 277/634
See application file for complete search history.

(56) References Cited

U.S. PATENT DOCUMENTS

| 5,921,232 | A * | 7/1999 | Yokoi et al. | 128/200.14 |
| 2004/0054262 | A1 * | 3/2004 | Horak | 600/300 |
| 2005/0193945 | A1 * | 9/2005 | Coffield et al. | 118/704 |

OTHER PUBLICATIONS

Krug, N. et al., "Validation of an enviormental exposure unit for controlled human inhalation studies with grass pollen in patients with seasonal allergic rhinitis." Clin. Exp Allergy., 2003, vol. 33, No. 12, p. 1667-1674.

* cited by examiner

*Primary Examiner* — Sally Merkling
(74) *Attorney, Agent, or Firm* — Browdy and Neimark, PLLC

(57) ABSTRACT

An antigen supply device 1 according to the present invention is mainly configured by a cylindrical member 3 extending in the vertical direction. An air suction port 5 for sucking the air in the antigen exposure chamber is provided at a lower end of the cylindrical member. An axial fan 6 that generates a flow of the air flowing upward in an axial direction of the cylindrical member is attached above the air suction port of the cylindrical member. Moreover, a supply port 4 through which high-concentration antigens are jetted from a dust feeder on the outside of the antigen exposure chamber is provided above the axial fan of the cylindrical member. The antigen supply device 1 is disposed near the outdoor air diffuser of the antigen exposure chamber, and configured to blow out high-concentration antigens, which are supplied from the dust feeder on the outside of the antigen exposure chamber, to the outdoor air diffuser 2 from an upper end of the cylindrical member after mixing the antigens with the air in the antigen exposure chamber sucked from the air suction port and diluting the antigens, and moreover mix the antigens with the outdoor air from the outdoor air diffuser to fill the antigen exposure chamber A with the mixture of the antigens and the outdoor air.

5 Claims, 6 Drawing Sheets

Figure 1

(A) SETTING METHOD (B) ANTIGEN CONCENTRATION DISTRIBUTION (PLANE FL+1,150)

MEASUREMENT POINTS: LPC1, LPC2, LPC3, LPC4

(A) SETTING METHOD

MEASUREMENT POINT: LPC1, LPC2, LPC3, LPC4

(B) ANTIGEN CONCENTRATION
DISTRIBUTION (PLANE FL+1,150)

Figure 5

(A) SETTING METHOD (B) ANTIGEN CONCENTRATION BUILD-UP RESULT

Figure 6

(A) SETTING METHOD (B) ANTIGEN CONCENTRATION BUILD-UP RESULT

ANTIGEN SUPPLY DEVICE

TECHNICAL FIELD

The present invention relates to an antigen supply device, and, more particularly to an antigen supply device for an antigen exposure chamber.

BACKGROUND ART

For researches and experiments or the like concerning diseases such as allergies, an antigen exposure chamber adapted to be supplied with a predetermined amount of antigens in order to expose a subject to the antigens is used. An antigen supply device is used to supply the antigens to this antigen exposure chamber. However, as shown in FIG. 1, a conventional antigen supply device is formed by a system for directly supplying antigens from a dust feeder into an antigen exposure chamber or supplying antigens into an air-conditioning duct and, moreover, cannot be cleaned by water. (See, for example, Non-Patent Document 1)

As described above, the conventional antigen supply device is, so to speak, an antigen supply device for only one-sidedly supplying antigens into a chamber and, therefore, antigen concentration in the chamber is non-uniform (see, a concentration distribution diagram in FIG. 1). Further, it is difficult to clean the antigen supply device when a type of antigens is changed. If antigens used before remain in the duct they scatter again, or if antigens adhering to the antigen supply device remain for a long period mold may grow on the antigens.

Moreover, in the conventional device, unless the inside of the device is sufficiently dried, humidity in an exposure chamber cannot be controlled during a later exposure operation. The antigens may adhere to drops of water and affect build-up of concentration in the chamber.

Furthermore, there is also a problem in that the antigens tend to adhere to the antigen supply device unless special measures are taken against static electricity.

[Patent Document 1]: None
[Non-Patent Document 1]: Ide: Development of a Cedar Pollen Scattering Device for Medical Researches, Kankyo Gijutsu, Vol. 32, No. 3, p. 33 to 37, 2003

DISCLOSURE OF THE INVENTION

Problem to be Solved by the Invention

The present invention has been devised for the purpose of providing an antigen supply device for supplying antigens to an antigen exposure chamber that solve the problems in the antigen supply device according to the conventional technique described above.

Means for Solving the Problem

In order to attain the object, an antigen supply device according to the present invention is disposed near an outdoor air diffuser of the antigen exposure chamber. And the antigen supply device configured to blow out high-concentration antigens, which are supplied from a dust feeder on the outside of the antigen exposure chamber, to the outdoor air diffuser after mixing the antigens with the air sucked from the antigen exposure chamber and diluting the antigens, and moreover mix the antigens with the outdoor air from the outdoor air diffuser to fill the antigen exposure chamber with the mixture of the antigens and the outdoor air.

In a specific configuration, an antigen supply device according to the present invention is mainly configured by a cylindrical member extending in the vertical direction. An air suction port for sucking the air in the antigen exposure chamber is provided at a lower end of the cylindrical member. An axial fan that generates a flow of the air flowing upward in an axial direction of the cylindrical member is attached above the air suction port of the cylindrical member. Moreover, a supply port through which high-concentration antigens are jetted from a dust feeder on the outside of the antigen exposure chamber is provided above the axial fan of the cylindrical member. The antigen supply device is disposed near the outdoor air diffuser of the antigen exposure chamber. And that configured to blow out high-concentration antigens, which are supplied from the dust feeder on the outside of the antigen exposure chamber, to the outdoor air diffuser from an upper end of the cylindrical member after mixing the antigens with the air in the antigen exposure chamber sucked from the air suction port and diluting the antigens, and moreover mix the antigens with the outdoor air from the outdoor air diffuser to fill the antigen exposure chamber with the mixture of the antigens and the outdoor air.

The antigen supply device according to the present invention may further include a cleaning water pipe for supplying cleaning water for cleaning the inside of the cylindrical member to the cylindrical member and a drain for the cleaning water for draining the cleaning water. It is preferable that cleaning water supply ports are provided in an upper part and a lower part of the cylindrical member to make it possible to efficiently clean the entire cylindrical member.

It is preferable that the supply port through which the high-concentration antigens are jetted from the dust feeder is provided at the upper end of the cylindrical member. One or plural kinds of antigens may be supplied.

Moreover, it is preferable that the cylindrical member is formed by a member made of metal or conductive resin in order to prevent adhesion of the antigens due to static electricity or the like.

It is preferable that the antigen supply device according to the present invention is set below the outdoor air diffuser of the antigen exposure chamber and in the center of the chamber. The antigen supply device according to the present invention may be suspended from a ceiling of the antigen exposure chamber by suspending rods or the like or may be set on a floor surface of the antigen exposure chamber.

Effects of the Invention

By adopting the configuration described above, with the antigen supply device according to the present invention, it is possible to obtain a more uniform antigen concentration distribution in the chamber in shorter build-up time than in the conventional device. Since the simple setting method is adopted, it is possible to easily change a setting location.

Moreover, since the device is configured by components made of metal or conductive resin, it is possible to prevent adhesion of the antigens due to static electricity.

Moreover, since the antigens can be washed away by cleaning with the cleaning water, the antigens do not adhere to and remain in the antigen supply device to scatter again or grow mold. Therefore, it is possible to quickly perform shift to exposure to a different kind of antigens. It is preferable that pure water is used as the cleaning water in order to prevent stains and dregs from remaining.

Furthermore, by adopting an axial fan that can be cleaned by water and is waterproof, it is possible to automatically dry the antigen exposure chamber by turning the fan after the water cleaning. Since it is possible to quickly dry the antigen exposure chamber by turning the axial fan, it is possible to quickly and accurately perform humidity control in the exposure chamber without being affected by residual moisture.

BRIEF DESCRIPTION OF THE DRAWINGS

FIG. 1 is a diagram showing a configuration, an arrangement, and an antigen concentration distribution of a conventional antigen supply device;

FIG. 5 is a diagram for comparing build-up times of an antigen concentration in an antigen exposure chamber in the case when the height of an antigen supply nozzle is changed and shows a case where the antigen supply nozzle is provided at an end of a lower part of the antigen supply device; and FIG. 6 is a diagram for comparing build-up times of an antigen concentration in an antigen exposure chamber in the case when the height of an antigen supply nozzle is changed and shows a case where the antigen supply nozzle is provided at an end of an upper part of the antigen supply device.

DESCRIPTION OF SYMBOLS 1, 1': Antigen supply devices,
A: Antigen exposure chamber,
2: Outdoor air diffuser,
3: Cylindrical duct,
4: Antigen supply nozzle,
5: Air suction port,
6: Axial fan,
7: Cleaning water supply pipe,
8: Solenoid valve,
9: Cleaning water jet nozzle,
10: Cleaning water drain,
11: Trap with antigen filtering device,
12: Suspending rods

BEST MODE FOR CARRYING OUT THE INVENTION

Figure 2:
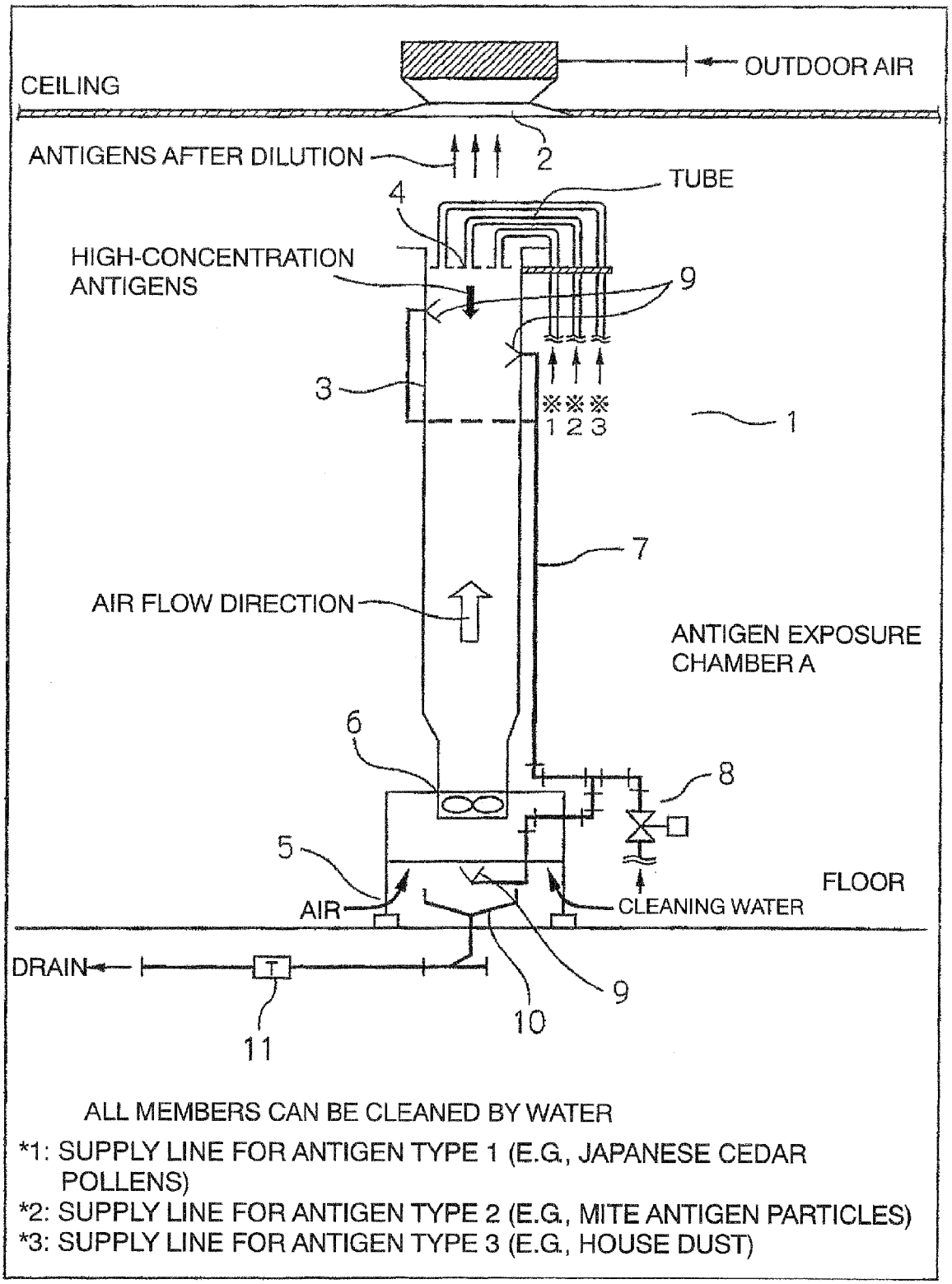
FIG. 2 is a configuration diagram of a first embodiment of an antigen supply device according to the present invention.
Figure 3:
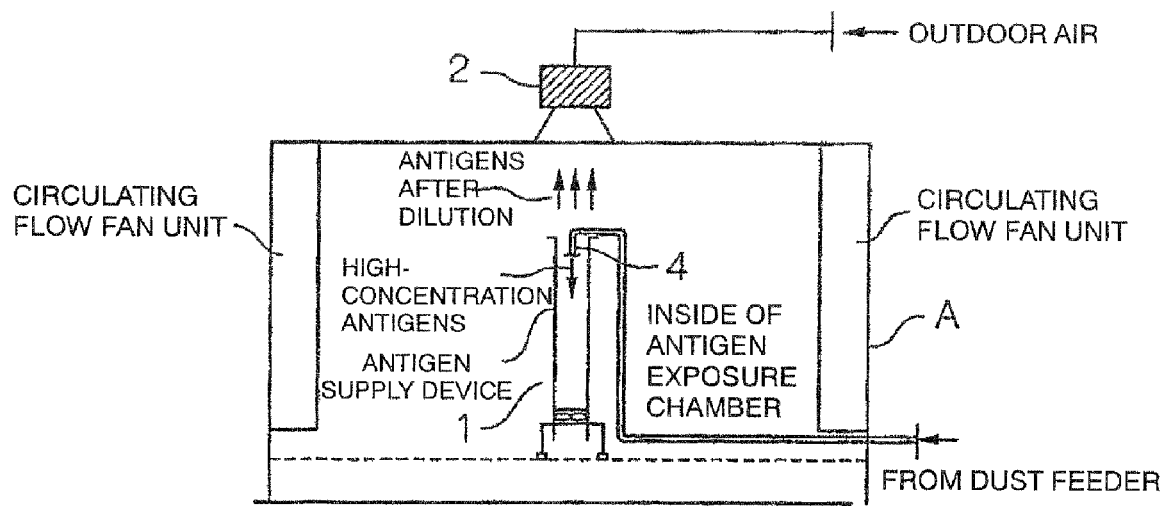
FIG. 3 is a diagram showing an arrangement and an antigen concentration distribution of the antigen supply device shown in FIG. 1.
Figure 3:
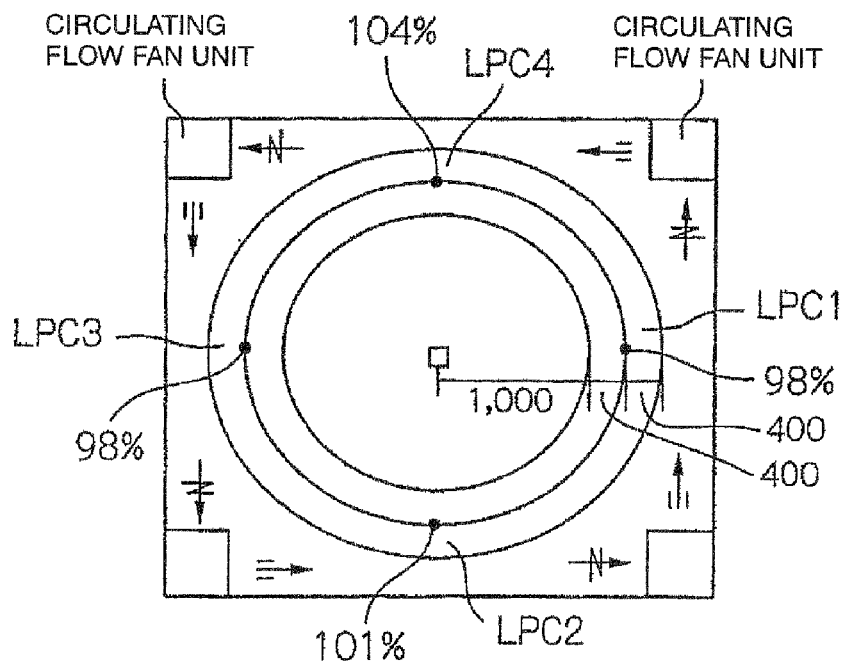

FIG. 2 is a sectional view showing a configuration of a first embodiment of an antigen supply device according to the present invention. FIG. 3 is an arrangement diagram showing a way that the antigen supply device according to this embodiment is set and a distribution diagram showing a concentration distribution of antigens in an antigen exposure chamber in the case when this device is used. The antigen supply device according to this embodiment is an antigen supply device of a type set on a floor surface of the antigen exposure chamber. As shown in FIG. 3, an antigen supply device 1 is set on a floor surface below an outdoor air diffuser 2 in substantially the center of an antigen exposure chamber A. As it is seen from the arrangement diagram of FIG. 3, high-concentration antigens supplied from a dust feeder provided on the outside of the antigen exposure chamber A are led in from an upper part of the antigen supply device 1. The antigens diluted and adjusted by the antigen supply device 1 are blown out from the antigen supply device, mixed with the outdoor air blown out from the outdoor air diffuser 2 of the antigen exposure chamber, and fills the entire antigen exposure chamber.

Details of the antigen supply device 1 are explained with reference to FIG. 2. As shown in FIG. 2, the antigen supply device 1 is configured in a long cylindrical shape extending vertically as a whole. A cylindrical duct 3 is provided in an upper part of the antigen supply device 1. High-concentration antigens (e.g., Japanese cedar pollens, mite antigen particles, or house dust) from the dust feeder provided on the outside of the antigen exposure chamber A are jetted and supplied downward from an antigen supply nozzle 4 provided at an upper end of the cylindrical duct 3. The cylindrical duct 3 is formed by metal, conductive resin, or the like to prevent the antigens such as Japanese cedar pollens from adhering thereto because of static electricity. On the other hand, an air suction port 5 is provided below the cylindrical duct 3 at an end in a lower part of the antigen supply device 1 and an axial fan 6 is provided above the air suction port 5 and at a lower end of the cylindrical duct 3. Therefore, a flow of the air flowing upward in a longitudinal direction in the antigen supply device 1 is formed by the rotation of the axial fan 6. The air in the antigen exposure chamber A is sucked into the antigen supply device 1 by the flow of the air through the air suction port 5. With such a configuration, in the cylindrical duct 3, an upward flow of the air in the antigen exposure chamber A through the air suction port 5 and a downward flow of the high-concentration antigens from the dust feeder through the antigen supply nozzle 4 collide with each other. The antigens are moderately mixed with the air and diluted. The air mixed with the antigens finally flows out from an upper part of the antigen supply device 1. The air containing the moderately diluted antigens flowing out from the upper part of the antigen supply device 1 is further mixed with the outdoor air led in from the outdoor air diffuser 2 provided in a ceiling surface of the antigen exposure chamber A above the antigen supply device 1 and fills the entire inside of the antigen exposure chamber A.

The antigen supply device 1 is further provided with a cleaning water supply pipe 7 for washing away the antigens and the like after use. As shown in the figure, the cleaning water supply pipe 7 is laid to blow out cleaning water, which is supplied from a cleaning water supply source (not shown), from cleaning water jet nozzles 9 provided at an upper and a lower end of the cylindrical duct 3 through the solenoid valve 8. Moreover, a cleaning water drain 10 for draining the cleaning water is provided at a lower end of the antigen supply device 1. The cleaning water drain 10 collects the cleaning water that has cleaned the antigen supply device and discharges the cleaning water to the outside of the antigen exposure chamber through the trap with antigen filtering device 11. With such a configuration, after the antigen exposure chamber A is used in an experiment or the like, it is possible to jet the cleaning water from the upper part and the lower part of the device through the cleaning water jet nozzles 9 to cleanly wash away the used antigens, subsequently, dry the antigen exposure chamber A by turning the axial fan 6, and quickly bring the antigen exposure chamber into a state in which the antigen exposure chamber can be used for the next experiment.

A distribution diagram shown in a lower part of FIG. 3 shows a concentration distribution of antigens at the time when the antigen supply device 1 shown in FIG. 2 is used in an arrangement shown in an upper part of FIG. 3. As it is evident from this distribution diagram, an antigen concentration distribution in the case when the antigen supply device according to the present invention is used is extremely uniform compared with the concentration distribution by the conventional antigen supplying method shown in a lower part of FIG. 1.

Figure 4:
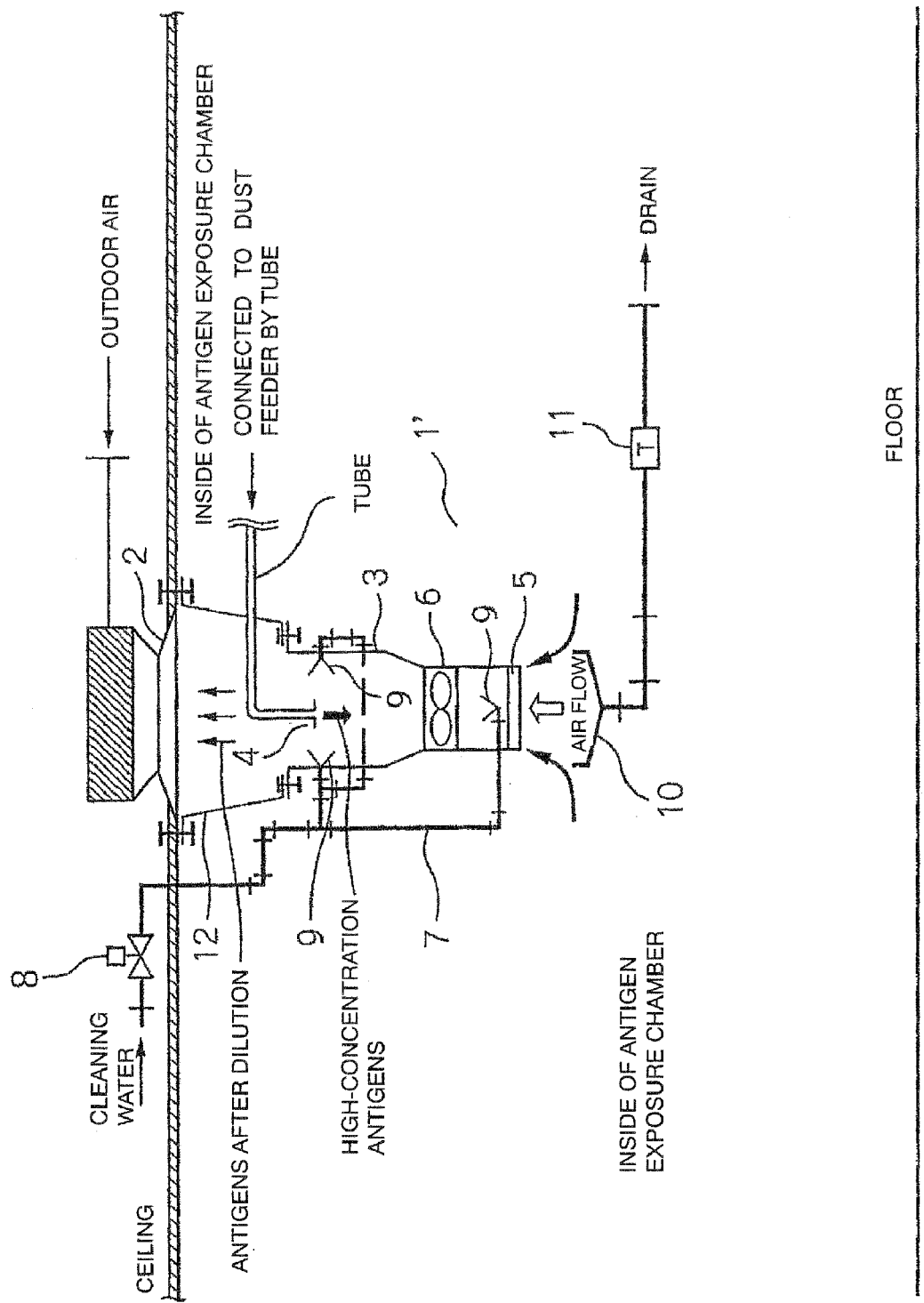
FIG. 4 is a configuration diagram of a second embodiment of the antigen supply device according to the present invention.

FIG. 4 is a sectional view showing a configuration of a second embodiment of the antigen supply device according to the present invention. In this embodiment, the antigen supply device is suspended from a ceiling of an antigen exposure chamber. As it is seen from the figure, an antigen supply device 1' is suspended below the outdoor air diffuser 2, which is provided in the ceiling of the antigen exposure chamber, via suspending rods 12. The suspending rods 12 are fixed to the cylindrical duct 3 of the antigen supply device 1'. Other components of the antigen supply device 1' are the same as those of the antigen supply device 1 shown in FIG. 2 and, therefore, denoted by reference numerals same as those shown in FIG. 2. Since functions of the components are also the same as those of the antigen supply device 1, explanation of the functions is omitted. The antigen supply device 1' is different from the antigen supply device 1 shown in FIG. 2 in that the cleaning water pipe 7 is laid from the ceiling. This is because the antigen supply device 1' is a ceiling suspension type. The entire antigen supply device 1' is shorter than the antigen supply device 1 shown in FIG. 2. This is for the purpose of reducing the weight of the antigen supply device 1' as much as possible because the antigen supply device 1' is the ceiling suspension type.

FIGS. 5 and 6 are diagrams for comparing build-up times of an antigen concentration in an antigen exposure chamber in the case when the height of an antigen supply nozzle is changed. FIG. 5 shows a case where the antigen supply nozzle is provided at an end of a lower part of the antigen supply device. FIG. 6 shows a case where the antigen supply nozzle is provided at an end of an upper part of the antigen supply device. As it is evident from graphs in lower parts of the respective diagrams, build-up of antigen concentration in the antigen exposure chamber takes time when a position of the antigen supply nozzle is low. Therefore, from the viewpoint of build-up of concentration, as described in the respective embodiments of the present invention, it is preferable to set the antigen supply nozzle in a position as high as possible.

Moreover, it is preferable to use, instead of the tap water, pure water as the cleaning water because the antigen exposure chamber can be cleanly washed without leaving any water stain.

INDUSTRIAL APPLICABILITY

The antigen supply device according to the present invention has been explained in detail with reference to the embodiments. However, the present invention is not limited to these embodiments and various alterations and modifications are possible within a range of a technical idea of the present invention.

For example, all antigens can be used as the antigens. It is preferable that the outdoor air diffuser of the antigen exposure chamber is in the center and the antigen supply device is provided right below the outdoor air diffuser. However, positions of the outdoor air diffuser and the antigen supply device do not have to be limited to this depending on the chamber structure.

The invention claimed is:

1. An antigen supply device for supplying antigens to an antigen exposure chamber having an outdoor air diffuser, comprising:
    a cylindrical member extending in a vertical direction and having an upper end and a lower end;
    an air suction port disposed at the lower end of the cylindrical member for sucking air in the antigen exposure chamber into the antigen supply device;
    an axial fan that generates a flow of air flowing upward in an axial direction of the cylindrical member being disposed within the cylindrical member at the lower end of the cylindrical member above the air suction port; and
    a supply port, through which high-concentration antigens are jetted from a dust feeder on the outside of the antigen exposure chamber downward into the cylindrical member, disposed in the cylindrical member between the upper end and the lower end of the cylindrical member, wherein
    the antigen supply device is disposed near the outdoor air diffuser of the antigen exposure chamber, and is configured to blow out high-concentration antigens, which are supplied from the dust feeder disposed on the outside of the antigen exposure chamber, toward the outdoor air diffuser from an upper end of the cylindrical member after mixing the antigens with the air in the antigen exposure chamber sucked from the air suction port and diluting the antigens, and moreover mix the antigens with outdoor air from the outdoor air diffuser to fill the antigen exposure chamber with the mixture of the antigens and the outdoor air.

2. The antigen supply device according to claim 1, further comprising:
    a cleaning water jet nozzle disposed within the cylindrical member at the upper end of the cylindrical member and a separate cleaning water jet nozzle disposed at the lower end of the cylindrical member for supplying cleaning water for cleaning the inside of the cylindrical member; and
    a drain, disposed below the lower end of the cylindrical member, for draining the cleaning water, and
    a trap with antigen filtering device disposed in the drain for preventing antigen contained within the cleaning water from flowing out to the outside of the antigen exposure chamber,
    wherein the inside of the cylindrical member is adapted to be cleaned by the cleaning water and thereafter to be quickly dried by turning the axial fan.

3. The antigen supply device according to claim 1, wherein the cylindrical member is formed by a member made of metal or conductive resin.

4. The antigen supply device according to claim 1, wherein the antigen supply device is suspended from a ceiling of the antigen exposure chamber or is set on a floor surface of the antigen exposure chamber.

5. The antigen supply device according to claim 2, wherein the cleaning water is not tap water but is a pure or purified water that does not leave water stains.

\* \* \* \* \*